United States Patent
Landeck

(12) 
(10) Patent No.: US 6,302,857 B1
(45) Date of Patent: Oct. 16, 2001

(54) METHOD AND APPARATUS FOR LOWERING AUDIBLE NOISE EMISSIONS FROM LITHOTRIPTORS

(76) Inventor: Vince Landeck, 609 Kipling Way, St. Charles, MO (US) 63304

( * ) Notice: Subject to any disclaimer, the term of this patent is extended or adjusted under 35 U.S.C. 154(b) by 0 days.

(21) Appl. No.: 09/587,134

(22) Filed: Jun. 2, 2000

(51) Int. Cl.[7] ..................................... A61H 1/00
(52) U.S. Cl. ............................. 601/4; 181/207
(58) Field of Search .................... 601/2, 4; 181/207, 181/208, 209, 210; 600/439

(56) References Cited

U.S. PATENT DOCUMENTS

| | | | |
|---|---|---|---|
| 5,259,383 | * 11/1993 | Holstein et al. | 128/660.01 |
| 5,598,051 | * 1/1997 | Frey | 310/334 |
| 5,689,572 | * 11/1997 | Ohki et al. | 381/71.3 |
| 6,179,792 | * 1/2001 | Krause | 601/2 |

FOREIGN PATENT DOCUMENTS 00-469-23 * 10/1992 (EP) ............................. F02B/77/13

* cited by examiner

*Primary Examiner*—Marvin M. Lateef
*Assistant Examiner*—Eleni Mantis Mercader
(74) *Attorney, Agent, or Firm*—Howell & Haferkamp, LC

(57) ABSTRACT

A noise dampening shroud is configured to surround the generator of lithotriptor device to reduce the noise emissions caused as a result of the generation of acoustic shock waves during extracorporeal treatment of a patient. The shroud comprises an insulating body and a cover. The insulating body comprises sound dampening insulation and is configured to surround substantially all of the housing that typically encases the generator of convention lithotriptors. The cover is comprised of a thin pliant material configured to surround the insulating body and is provided with fasteners for removably securing the insulating body to the generator. When attached to the generator of a lithotriptor device, the shroud greatly reduces the noise emitting by the generation of acoustic shock waves and thereby minimizes the distraction and disturbance caused by such noise.

20 Claims, 2 Drawing Sheets

METHOD AND APPARATUS FOR LOWERING AUDIBLE NOISE EMISSIONS FROM LITHOTRIPTORS

BACKGROUND OF THE INVENTION

This invention relates generally to lithotriptor devices, and more particularly, to audible noise emissions from acoustic shock wave generators of such devices.

Lithotriptors are devices employed in medical and therapeutic extracorporeal treatment of humans and animals for the destruction of concretions (e.g. kidney stones), induction of bone growth, and treatment of other soft-tissues. These devices operate by producing focused acoustic shock waves capable of creating extremely high pressure differentials at localized regions within a patient's body that act upon targeted concretions or bodily tissue being treated.

Various types of lithotriptors utilize different means for producing acoustic shock waves. Such means are known in the art and include electromagnetic, piezoelectric, and electrical spark-gap generators. While the type of generator used to produce the acoustic shock waves varies from one lithotriptor to the next, each type of generator ultimately produces acoustic shock waves capable of being focused in a specific trajectory and at a certain depth.

Because the focal point or isocenter of a conventional shock wave generator is fixed, the generator of a conventional lithotriptor is typically encased in a housing suspended from a moveable arm such that the trajectory of the acoustic shock waves can be aligned relative to a patient receiving treatment. While the movable arm of the lithotriptor allows alignment of the shock wave trajectory, the depth of the shock wave within the patient's body is controlled by expansion and contraction of a fluid-filled cushion that extends through the housing and engages the patient's epidermis.

In addition to the arm and fluid-filled cushion extending from the generator housing, conventional lithotriptors may include a fluid supply line or hose extending from the housing to provide means for liquid cooling of the generator. Furthermore, the housing may have one or more mechanisms for aligning the isocenter of the acoustic shock waves relative to the patient.

Although lithotriptor devices have proven useful in medical treatment and therapy, such devices produce a significant amount of unfocused noise when generating the acoustic shock waves. Such noise results from the discharge of capacitors, generation of sparks, or other means used to create the acoustic shock waves.

In addition to disturbing those present in a room in which the device is being used, the audible noise emissions of the lithotriptors have been known to distract and disturb persons in adjacent or nearby rooms. This is especially problematic in modern operating rooms that often share a common sterile hallway with little or no means of preventing sound transfer between adjacent rooms. In such situations, noise generated by use of lithotriptor can disturb medical personnel performing intricate surgery in adjacent rooms.

SUMMARY OF THE INVENTION

Among the advantages of the present invention may be noted the provision of a noise dampener for reducing the audible noise emissions produced by the acoustic shock wave generator of a lithotriptor device, and the provision of a method of reducing the audible noise emitted from such a device.

In general, a noise dampener of the present invention comprises a shroud of sound dampening insulation configured and adapted to surround the acoustic shock wave generator of a lithotriptor device without interfering with the operation of the device. The shroud is connected to the generator and significantly reduces the noise emissions caused by the generation of acoustic shock waves when the lithotriptor is in use.

The preferred embodiment of the present invention is a removable shroud that can be repeatedly attached to, and removed from, the generator without damaging the shroud and without modification of the lithotriptor. The removability of the shroud of the preferred embodiment allows the shroud to be removed when utilizing alignment mechanisms or other similar devices that would otherwise be covered by the shroud when the lithotriptor is in use.

Another aspect of the present invention is a method of reducing the audible noise emitted from the generator of a lithotriptor device. The method comprises surrounding the generator with sound dampening insulation without interfering with the operation of the lithotriptor.

Other features and advantages will be in part apparent and in part pointed out hereinafter.

BRIEF DESCRIPTION OF THE DRAWINGS

Corresponding reference characters indicate corresponding parts throughout the several views of the drawings.

DESCRIPTION OF THE PREFERRED EMBODIMENT

Figure 1:
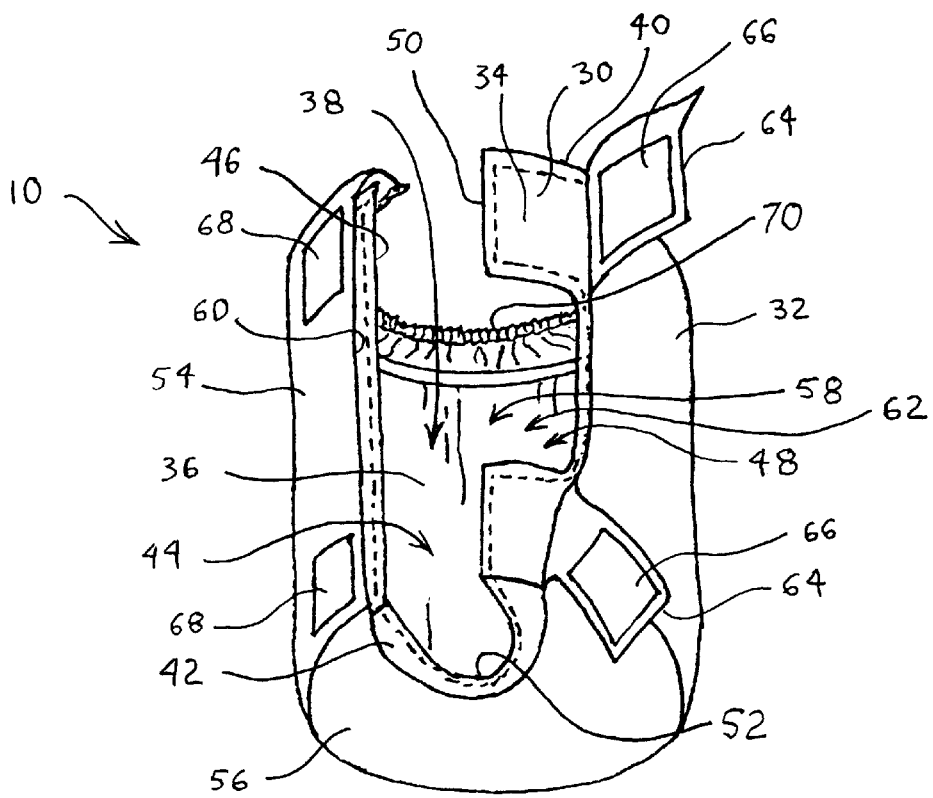
FIG. 1 is an isometric view of a shroud of the present invention showing an insulated body surrounded by a cover.

Referring now to the drawings, and first more particularly to FIG. 1, a shroud of the present invention is indicated in its entirety by the reference numeral 10. The purpose of the shroud 10 is to reduce the audible noise emitted from a generator of a lithotriptor as it produces acoustic shock waves during extracorporeal treatment.

For purposes of describing the preferred embodiment of the invention, it is necessary to first describe the generator of the lithotriptor for which the shroud 10 is preferably configured and adapted for use. However, it should be understood that the invention is not limited to use with a specific type or model of lithotriptor and one skilled in the art, having knowledge of the present disclosure, could practice the invention in connection with various lithotriptor devices.

Figure 3:
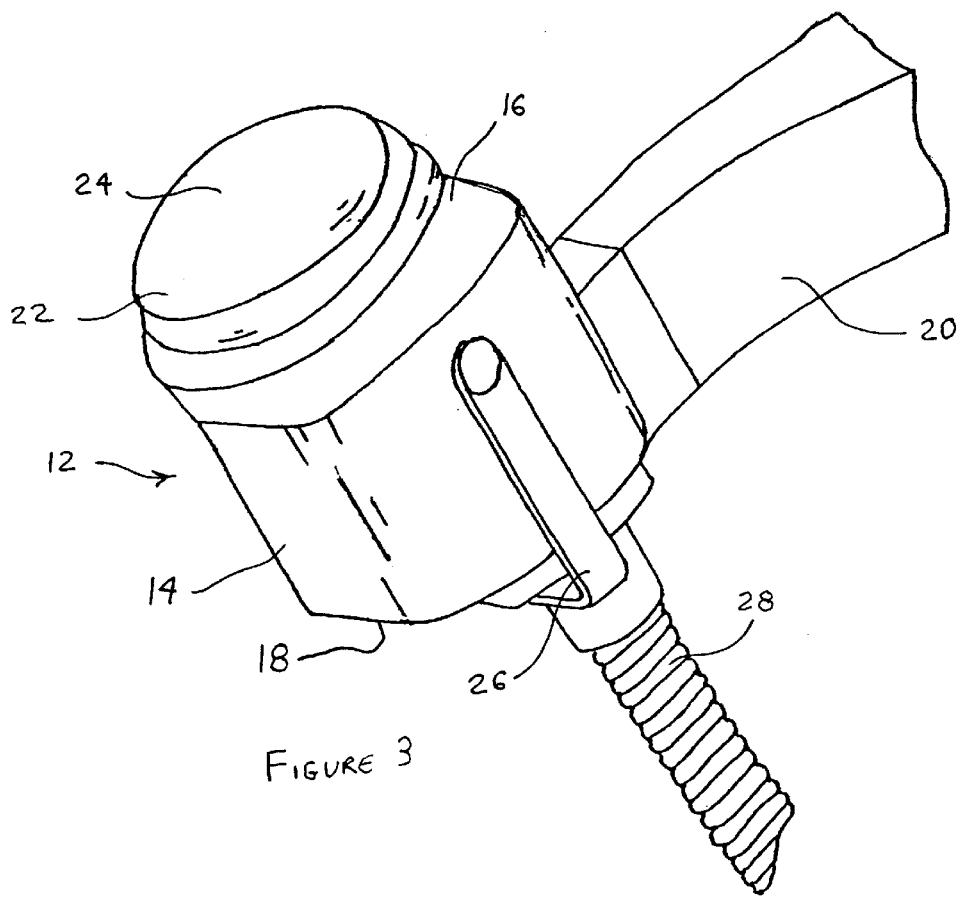
FIG. 3 is a partial isometric view of a conventional lithotriptor device.
Figure 4:
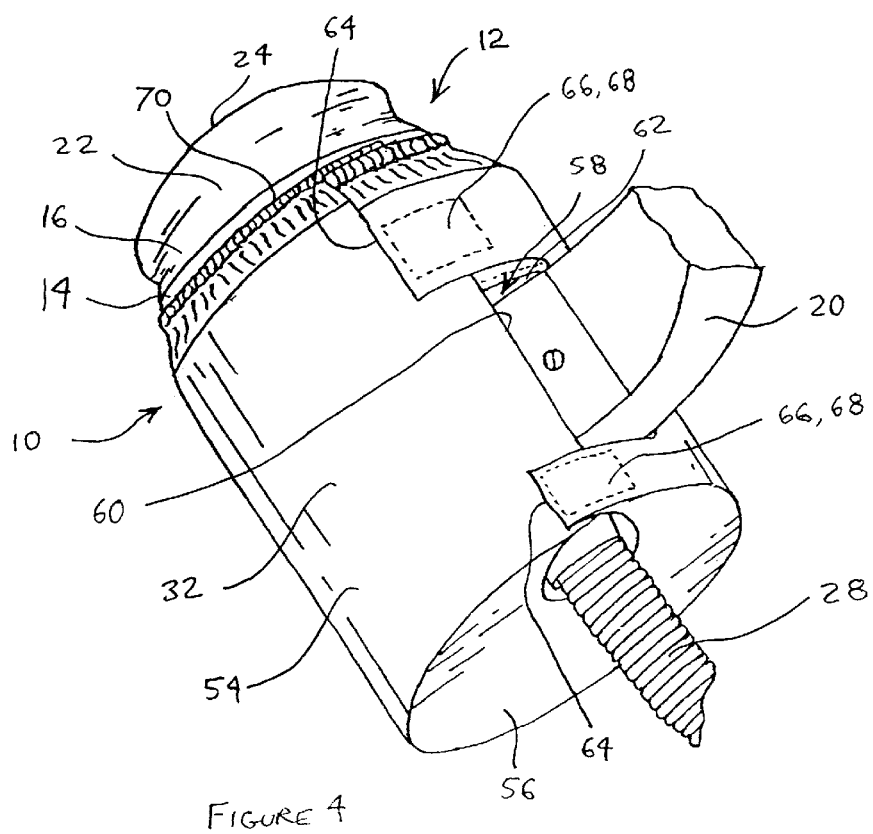
FIG. 4 is a partial isometric view showing the shroud of FIG. 1 attached to the lithotriptor device of FIG. 3.

The shroud 10 shown in this embodiment is preferably adapted and configured for use with a LITHOSTAR® MODULARIS® lithotriptor manufactured by Siemens Medical Systems, Inc. and shown in part in FIGS. 3 and 4. As shown in the figures, the generator of the lithotriptor, generally indicated at 12, is encased by a generally cylindrical housing 14 and has an opposite top 16 and bottom 18. A moveable arm 20 extending radially from the housing 14 supports the generator 12 and connects the generator to the remainder of the lithotriptor device (not shown). The movable arm 20 allows for positioning of the generator 12 relative to a patient (not shown) receiving treatment to align the trajectory of the acoustic shock waves with the intended target. The depth of the shock wave isocenter within the patient's body is controlled by a fluid-filled cushion 22 at the top 16 of the generator 12 that extends through the housing 14 and has an exterior transmission surface 24 configured to transmit the acoustic shock waves into a patient's body by engaging the patient's epidermis.

The specific lithotriptor described herein also incorporates an aligning mechanism 26 pivotally mounted to the housing 12. When desired, the aligning mechanism 26 may be swung above the top 16 of the generator 12 for producing a focus phantom to facilitate proper positioning of the isocenter of the acoustic shock waves via x-ray imaging. During treatment, the alignment mechanism 26 is swung beneath the bottom 18 of the generator 12 where it will not interfere with the operation of the lithotriptor.

The generator 12 of the lithotriptor also has a fluid supply line 22 extending from the bottom 18 of the housing 14 for liquid cooling of the generator 12 when the lithotriptor is in use. As shown, the fluid supply line 28 is in the form of a flexible hose to accommodate positional movement of the generator 12.

The shroud 10 of the invention preferably comprises an insulating body, generally indicated at 30, and a cover generally indicated at 32. The insulating body 30 comprises sound dampening insulation that is preferably in the form of a fibrous pad of the type disclosed in U.S. Pat. No. 5,952, 248, the disclosure of which is incorporated herein by reference. However, it should be noted that the sound dampening insulation could also be formed from other suitable materials known in the art for use as acoustic insulators, in place of or in conjunction with fibrous padding. A cladding 34 of vinyl or other suitable material is preferably sewn around or otherwise attached to the insulating body 30 to reduce wear of the sound dampening insulation and facilitate cleaning of the insulating body.

The insulating body 30 is preferably formed as a single piece in a shape configured and adapted to substantially surround the housing 14 of the generator 12 without obstructing the fluid-filled cushion 22 at the top 16 of the generator. As shown by itself in FIG. 2, the insulating body 30 has a generally cylindrical wall 36 defining an inner cavity 38. A top edge 40 of the cylindrical wall 36 forms a mouth to the inner cavity 38 while the opposite bottom of the inner cavity is substantially closed by a generally disk-shaped wall 42 of the insulating body 30.

A slot 44 passes through both the cylindrical wall 36 and disk-shaped wall 42 of the insulating body 30 and preferably extends axially from the top edge 40 of the insulating body. The slot 44 preferably has a straight first edge 46 and a notch 48 formed in an opposite second edge 50. A concave semicircular edge of the disk-shaped wall 42 joins the opposite first 46 and second 50 edges and forms a closed end 52 of the slot 44.

The configuration of the insulating body 30 described above allows the insulating body to be slid onto the housing 14 of the generator 12 by placing the insulator body over the generator such that generator is received in the inner cavity 38 of the insulating body with the arm 20 and the fluid supply line 28 of the lithotriptor extending through the slot 44. When the insulating body 30 is properly positioned around the housing 14, the bottom 18 of the generator 12 is adjacent the disk-shaped wall 42 of the insulating body 30 with the fluid supply line 28 extending through the closed end 52 of the slot 44 and the arm 20 of the lithotriptor extending through the notch 48 of the slot. In such a position, the cover 14 of the shroud 10 may then be used to removably secure the insulating body 30 around the generator 12 of the lithotriptor.

The cover 32 of the shroud 10 as shown in FIGS. 1 and 4 is preferably comprised of a pliant material such as vinyl and is preferably similar in shape to the insulating body 30. Like the insulating body 30, the cover 32 preferably has a cylindrical portion 54, a disk-shaped portion 56, and a slot 58. Furthermore, like the slot 44 of the insulating body 30, the slot 58 of the cover 32 has a straight first edge 60 and a notch 62 in an opposite second edge 64.

Unlike the slot 44 of the insulating body 30, the second edge 64 of the slot 58 of the cover 32 is configured to overlap the first edge 60. Two fastener mechanisms 66, preferably comprising VELCRO® fasteners sewn to the cover 32, are positioned adjacent the second edge 64 of the slot 58 on either side of the notch 62. The fastener mechanisms 66 adjacent the second edge 64 of the slot 58 are configured to engage corresponding fastener mechanisms 68 adjacent the opposite first edge 60 to removably secure the opposite edges of the slot together. Finally, unlike the insulating body 30, the cover 32 has an elastic member sewn into a top edge 70 of the cover that acts to constrict the top edge, drawing the top edge radially inward.

With the insulating body 30 positioned around the housing 14 of the generator 12 as described above, the cover 32 can be slid over the insulating body in a manner similar to the way the insulating body is slid over the housing. With the cover 32 in place around the insulating body 30, the fastener mechanisms 66 adjacent the second edge 64 of the slot 58 of the cover can be secured to the corresponding fastener mechanisms 68 adjacent the opposite first edge 60 of the slot, as shown in FIG. 4. By securing the fastener mechanisms 66, 68 to each other, the cover 32 conforms around the arm 20 and the fluid supply line 28 of the lithotriptor, and closes the remainder of the slot 58. Additionally, the diameter of the cylindrical portion 54 of the cover 32 is dimensioned such that the cover squeezes the insulating body 30 to bring the first 46 and second 50 edges of the slot 44 of the insulating body toward each other. Finally, the elastic member of the top edge 70 of the cover 32 holds the top portion of the cover flush adjacent the top 16 of the housing 14 of the generator 12.

Preferably, the shroud 10 is shaped, configured, and of a suitable material such that noise emissions from the housing 14 during operation of the generator 12 are dampened by at least a factor of five (e.g. 7 dB), and more preferably by at least a factor of ten (e.g. 10 dB), and yet more preferably by a factor of at least 20 (e.g. 13 dB) relative to undampened noise emissions. Furthermore, the shroud 10 can quickly and easily be removed and reattached to the housing 14 to facilitate use of the aligning mechanism 26 and service of the generator 12 without damaging the shroud.

In view of the above, it will be seen that several objects of the invention are achieved and advantageous results obtained.

As various changes could be made in the above construction without departing from the scope of the invention, it is intended that all matter contained in the above description or shown in the accompanied drawings shall be interpreted as illustrative and not in a limited sense.

What is claimed is:

1. A noise dampener for use with a lithotriptor having an acoustic shock wave generator, the shock wave generator including an exterior housing and an exterior transmission surface for transmitting acoustic shock waves to a patient during treatment of the patient, the noise dampener comprising:

a shroud comprising sound dampening insulation adapted for connecting to the generator, the shroud being adapted to closely surround substantially all of the housing of the generator, the shroud further being adapted to reduce audible noise emissions of the generator without obstructing the transmission of acoustic shock waves to the patient during treatment when the shroud is connected to the generator.

2. The noise dampener of claim 1, wherein:

the shroud is adapted to be repeatedly attached to and removed from the generator without damaging the shroud.

3. The noise dampener of claim 2, wherein:

the shroud comprises an insulating body and a cover, the insulating body comprising the sound dampening insulation and the cover comprising a pliant material, the insulating body being configured to cover at least a portion of the generator in a manner for reducing the audible noise emissions of the generator, the cover being configured to surround at least a portion of the insulating body and having at least one fastener mechanism for securing a first portion of the cover to a second portion of the cover in a manner that allows the insulating body to be supported by the generator.

4. The noise dampener of claim 2, wherein:

the shroud has an open inner cavity and a mouth in communication with the inner cavity, the shroud being adapted for being slid at least partially around the generator in a manner such that the generator is received into the inner cavity via the mouth of the shroud as the shroud is being connected to the generator.

5. The noise dampener of claim 4 for use with the shock wave generator, the shock wave generator further having a support arm protruding from the housing, wherein:

the shroud has a through slot for extension therethrough of the arm of the generator at a given location of the slot when the shroud is connected to the generator, the slot extending from the mouth of the shroud such that the arm of the generator can pass along the slot from the mouth to the given location of the slot without the arm interfering with the positioning of the portion of the housing in the inner cavity of the shroud as the shroud is being connected to the generator.

6. The noise dampener of claim 5 for use with the shock wave generator, the shock wave generator further having a fluid supply line protruding from the housing, wherein:

the slot of the shroud is shaped and adapted to allow the fluid supply line of the generator to extend therethrough when the shroud is connected to the generator and such that the fluid supply line will not interfere with the positioning of the portion of the housing in the inner cavity of the shroud as the shroud is being connected to the generator.

7. The noise dampener of claim 5, wherein:

the shroud is pliant such that the shroud can be deformed when the portion of the housing is being positioned in the inner cavity of the shroud.

8. The noise dampener of claim 1, wherein:

the sound dampening insulation comprises fibrous padding.

9. The noise dampener of claim 1, wherein:

the shroud will reduce audible noise emissions of the generator by at least approximately 7 dB when the shroud is connected to the generator.

10. The noise dampener of claim 1, wherein:

the shroud will reduce audible noise emissions of the generator by at least approximately 10 dB when the shroud is connected to the generator.

11. The noise dampener of claim 1, wherein:

the shroud will reduce audible noise emissions of the generator by at least approximately 13 dB when the shroud is connected to the generator.

12. A noise dampened lithotriptor comprising:

a lithotriptor having an acoustic shock wave generator, the shock wave generator including an exterior housing and an exterior transmission surface for transmitting acoustic shock waves to a patient during treatment of the patient; and a shroud comprising sound dampening insulation connected to the generator of the lithotriptor, the shroud closely surrounding substantially all of the housing of the generator, the shroud further being adapted to reduce audible noise emissions of the generator without obstructing the transmission of the acoustic shock waves to the patient during treatment.

13. The noise dampened lithotriptor of claim 12 wherein:

the shroud is adapted and configured such that the shroud reduces audible noise emissions of the generator by at least approximately 10 dB.

14. The noise dampened lithotriptor of claim 12 wherein:

the shroud comprises an insulating body and a cover, the insulating body comprising the sound dampening insulation and the cover comprising a pliant material, the insulating body covering at least a portion of the generator in a manner that reduces the audible noise emissions of the generator, the cover surrounding at least a portion of the insulating body and having at least one fastener mechanism for securing a first portion of the cover to a second portion of the cover in a manner that supports the insulating body by the generator.

15. A method of dampening noise emissions of a lithotriptor device, the method comprising:

providing a lithotriptor device having a shock wave generator; and surrounding a portion of the generator with sound dampening insulation in a manner to dampen noise emissions from the generator.

16. The method of claim 15, wherein:

the sound dampening insulation dampens noise emissions from the generator by at least approximately 7 dB.

17. The method of claim 15, wherein:

the sound dampening insulation comprises fibrous padding.

18. The method of claim 15, wherein:

the step of providing a lithotriptor includes providing a lithotriptor having a housing surrounding the generator.

19. The method of claim 18, wherein: the step of surrounding the generator with sound dampening insulation comprises surrounding the housing with the sound dampening insulation.

20. The method of claim 19, wherein:

the step of surrounding the generator with sound dampening insulation includes forming a shroud comprised of sound dampening insulation that can be repeatedly attached to, and removed from, the generator without damaging the shroud.

* * * * *

UNITED STATES PATENT AND TRADEMARK OFFICE
CERTIFICATE OF CORRECTION

| | | |
|---|---|---|
| PATENT NO. | : 6,302,857 B1 | Page 1 of 6 |
| APPLICATION NO. | : 09/587134 | |
| DATED | : October 16, 2001 | |
| INVENTOR(S) | : Landeck | |

It is certified that error appears in the above-identified patent and that said Letters Patent is hereby corrected as shown below:

The title page showing the illustrative figure should be deleted to be replaced with the attached title page.

The drawing sheets, consisting of Figs. 1-4, should be deleted to be replaced with the drawing sheets, consisting of Figs. 1-4, as shown on the attached page.

Figure 2:
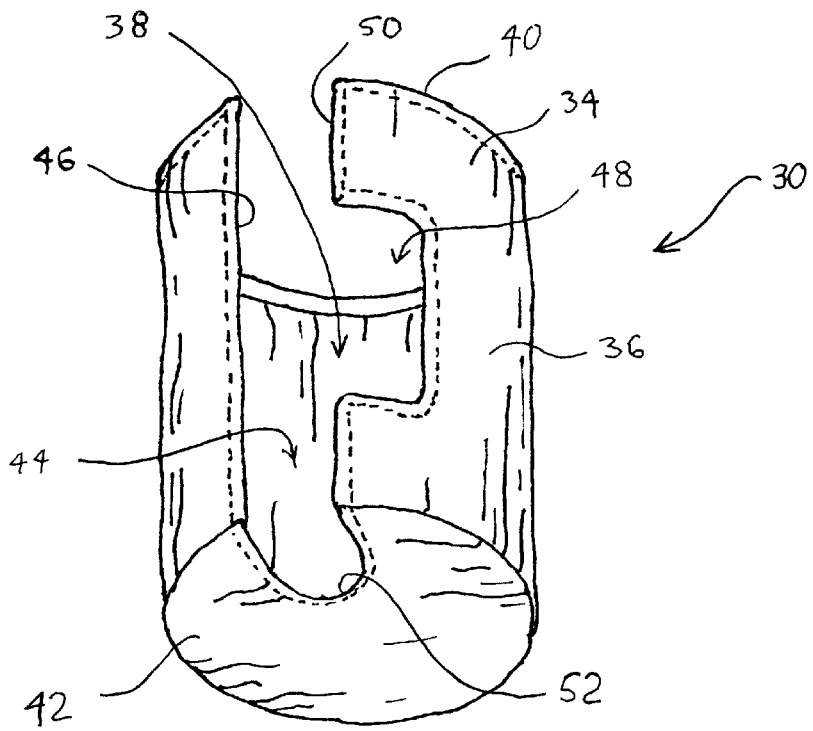
FIG. 2 is an isometric view of the insulating body of FIG. 1 shown by itself.

Please insert these new drawings, Figure 1 is on this title page attached and fig. 2, 3 & 4 are on these drawing sheets that are illustrated.

(12) United States Patent
Landeck

(10) Patent No.: US 6,302,857 B1
(45) Date of Patent: Oct. 16, 2001

(54) METHOD AND APPARATUS FOR LOWERING AUDIBLE NOISE EMISSIONS FROM LITHOTRIPTORS

(76) Inventor: Vince Landeck, 609 Kipling Way, St. Charles, MO (US) 63304

( * ) Notice: Subject to any disclaimer, the term of this patent is extended or adjusted under 35 U.S.C. 154(b) by 0 days.

(21) Appl. No.: 09/587,134

(22) Filed: Jun. 2, 2000

(51) Int. Cl.$^7$ .................................................. A61H 1/00
(52) U.S. Cl. ........................................ 601/4; 181/207
(58) Field of Search ........................... 601/2, 4; 181/207, 181/208, 209, 210; 600/439

(56) References Cited

U.S. PATENT DOCUMENTS 5,259,383 * 11/1993 Holstein et al. ............... 128/660.01
5,598,051 * 1/1997 Frey ................................... 310/334
5,689,572 * 11/1997 Ohki et al. ........................ 381/71.3
6,179,792 * 1/2001 Krause ................................ 601/2

FOREIGN PATENT DOCUMENTS 00-469-23 * 10/1992 (EP) ................... F02B/77/13

* cited by examiner

Primary Examiner—Marvin M. Lateef
Assistant Examiner—Eleni Mantis Mercader
(74) Attorney, Agent, or Firm—Howell & Haferkamp, LC

(57) ABSTRACT

A noise dampening shroud is configured to surround the generator of lithotriptor device to reduce the noise emissions caused as a result of the generation of acoustic shock waves during extracorporeal treatment of a patient. The shroud comprises an insulating body and a cover. The insulating body comprises sound dampening insulation and is configured to surround substantially all of the housing that typically encases the generator of convention lithotriptors. The cover is comprised of a thin pliant material configured to surround the insulating body and is provided with fasteners for removably securing the insulating body to the generator. When attached to the generator of a lithotriptor device, the shroud greatly reduces the noise emitting by the generation of acoustic shock waves and thereby minimizes the distraction and disturbance caused by such noise.

20 Claims, 2 Drawing Sheets

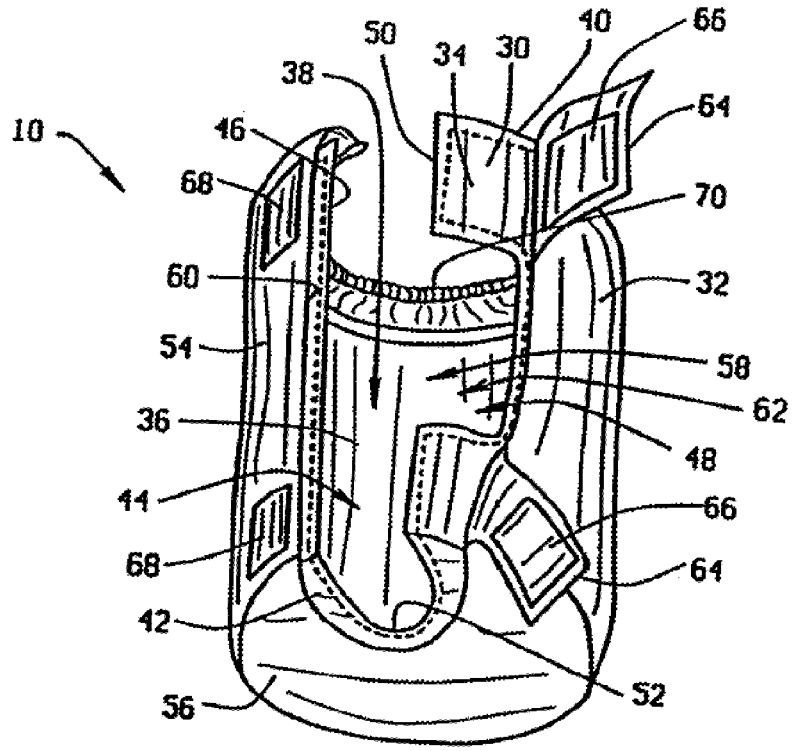

UNITED STATES PATENT AND TRADEMARK OFFICE
CERTIFICATE OF CORRECTION

| | | |
|---|---|---|
| PATENT NO. | : 6,302,857 B1 | Page 3 of 6 |
| APPLICATION NO. | : 09/587134 | |
| DATED | : October 16, 2001 | |
| INVENTOR(S) | : Landeck | |

It is certified that error appears in the above-identified patent and that said Letters Patent is hereby corrected as shown below:

On Drawing Sheet 1, informal Figure 1 is replaced with the formal Figure 1 shown here.

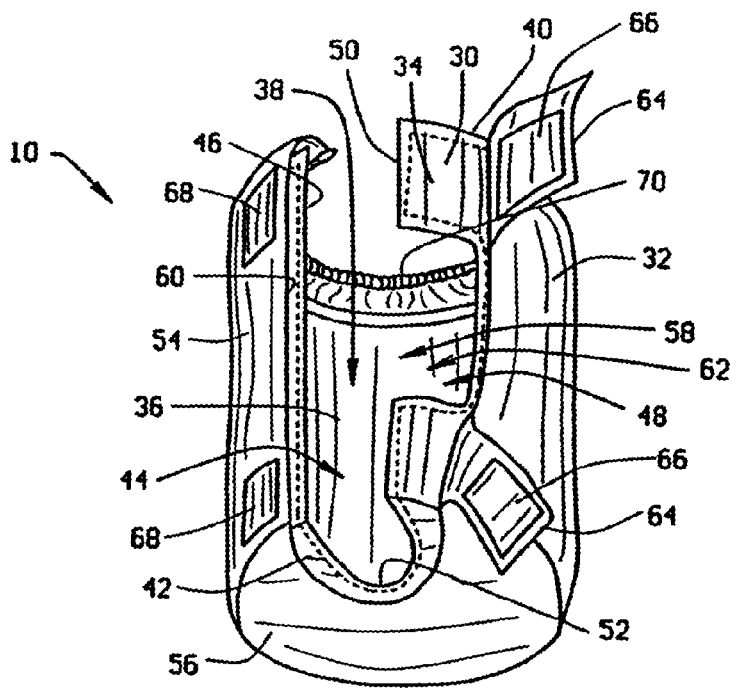

FIG. 1

UNITED STATES PATENT AND TRADEMARK OFFICE
CERTIFICATE OF CORRECTION

| | | |
|---|---|---|
| PATENT NO. | : 6,302,857 B1 | Page 4 of 6 |
| APPLICATION NO. | : 09/587134 | |
| DATED | : October 16, 2001 | |
| INVENTOR(S) | : Landeck | |

It is certified that error appears in the above-identified patent and that said Letters Patent is hereby corrected as shown below:

On Drawing Sheet 1, informal Figure 2 is replaced with the formal Figure 2 shown here.

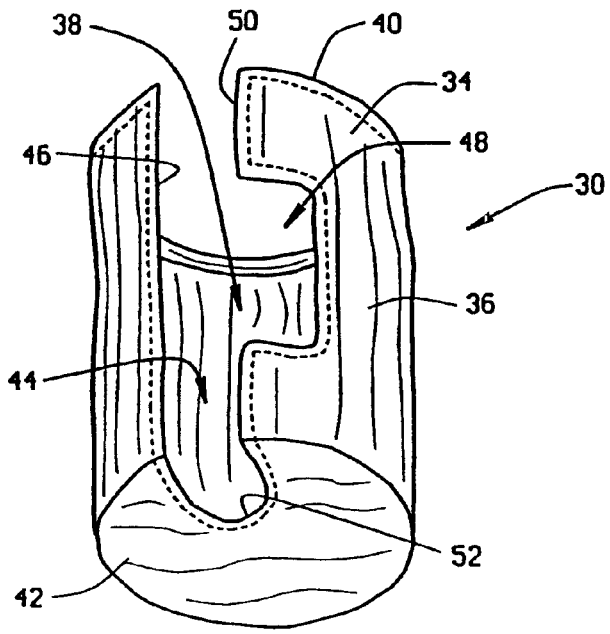

FIG. 2

UNITED STATES PATENT AND TRADEMARK OFFICE
CERTIFICATE OF CORRECTION

PATENT NO. : 6,302,857 B1  Page 5 of 6
APPLICATION NO. : 09/587134
DATED : October 16, 2001
INVENTOR(S) : Landeck It is certified that error appears in the above-identified patent and that said Letters Patent is hereby corrected as shown below:

On Drawing Sheet 2, informal Figure 3 is replaced with the formal Figure 3 shown here.

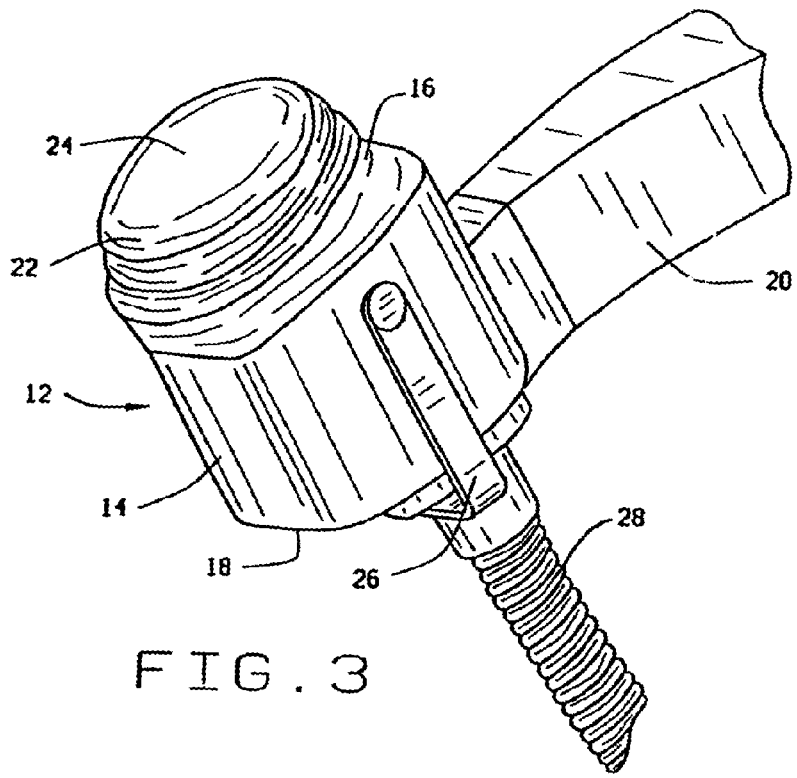

FIG. 3

UNITED STATES PATENT AND TRADEMARK OFFICE
CERTIFICATE OF CORRECTION

PATENT NO.        : 6,302,857 B1                           Page 6 of 6
APPLICATION NO.   : 09/587134
DATED             : October 16, 2001
INVENTOR(S)       : Landeck It is certified that error appears in the above-identified patent and that said Letters Patent is hereby corrected as shown below:

On Drawing Sheet 2, informal Figure 4 is replaced with the formal Figure 4 shown here.

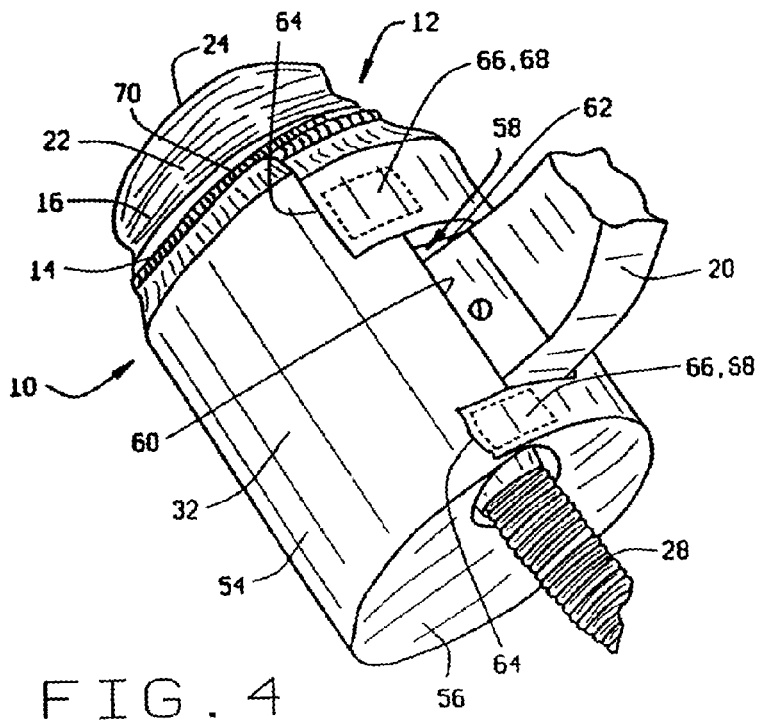

FIG. 4

Signed and Sealed this

Eighth Day of July, 2008

JON W. DUDAS
*Director of the United States Patent and Trademark Office*